United States Patent
Mantell et al.

(10) Patent No.: US 6,905,489 B2
(45) Date of Patent: Jun. 14, 2005

(54) LAPAROSCOPIC INSERTION DEVICE

(75) Inventors: Robert R. Mantell, Arlington Heights, IL (US); Peter A. Manzie, Berwyn, IL (US)

(73) Assignee: Northgate Technologies, Inc., Elgin, IL (US)

( * ) Notice: Subject to any disclaimer, the term of this patent is extended or adjusted under 35 U.S.C. 154(b) by 330 days.

(21) Appl. No.: 09/841,125

(22) Filed: Apr. 24, 2001

(65) Prior Publication Data

US 2002/0183715 A1 Dec. 5, 2002

(51) Int. Cl.[7] .............................................. A61M 31/00
(52) U.S. Cl. ........................ 604/506; 604/43; 604/508; 600/3
(58) Field of Search .............................. 600/3; 604/506, 604/43, 523, 508, 45

(56) References Cited

U.S. PATENT DOCUMENTS

| | | |
|---|---|---|
| 1,527,291 A | 2/1925 | Zorraquin |
| 2,623,521 A | 12/1952 | Shaw |
| 2,630,803 A | 3/1953 | Baran |
| 3,068,739 A | 12/1962 | Hicks, Jr. et al. |
| 3,530,492 A | 9/1970 | Ferber |
| 3,817,251 A | 6/1974 | Hasson |
| 3,840,008 A | 10/1974 | Noiles |
| 3,941,121 A | 3/1976 | Olinger et al. |
| 3,982,533 A | 9/1976 | Wiest |
| 4,177,814 A | 12/1979 | Knepshield et al. |
| 4,180,068 A | 12/1979 | Jacobsen et al. |
| 4,254,762 A | 3/1981 | Yoon |
| 4,269,192 A | 5/1981 | Matsuo |
| 4,299,230 A | 11/1981 | Kubota |
| 4,311,138 A | 1/1982 | Sugarman |
| 4,535,773 A | 8/1985 | Yoon |
| 4,550,715 A | 11/1985 | Santangelo et al. |
| 4,624,243 A | 11/1986 | Lowery et al. |
| 4,653,475 A | 3/1987 | Seike et al. |
| 4,869,717 A | 9/1989 | Adair |
| 5,098,388 A | 3/1992 | Kulkashi et al. |
| 5,104,381 A | 4/1992 | Gresl et al. |
| 5,137,509 A | 8/1992 | Freitas |
| 5,139,485 A | 8/1992 | Smith et al. |
| 5,199,944 A | 4/1993 | Cosmescu |
| 5,226,426 A | 7/1993 | Yoon |
| 5,246,426 A | 9/1993 | Lewis et al. |
| 5,256,148 A | 10/1993 | Smith et al. |
| 5,261,891 A | 11/1993 | Brinkerhoff et al. |
| 5,292,310 A | 3/1994 | Yoon |
| 5,421,821 A | 6/1995 | Janicki et al. |
| 5,514,087 A | 5/1996 | Jones |
| 5,514,111 A | 5/1996 | Phelps |
| 5,669,883 A | 9/1997 | Scarfone et al. |
| 5,676,156 A | 10/1997 | Yoon |
| 5,695,462 A | 12/1997 | Sutcu et al. |
| 5,707,362 A | 1/1998 | Yoon |
| 5,779,680 A | 7/1998 | Yoon |
| 5,807,402 A | 9/1998 | Yoon |
| 5,810,866 A | 9/1998 | Yoon |
| 5,827,221 A | 10/1998 | Phelps |
| 5,827,315 A | 10/1998 | Yoon |
| 5,882,340 A | 3/1999 | Yoon |
| 5,964,223 A | 10/1999 | Baran |

Primary Examiner—Thor S. Campbell
(74) Attorney, Agent, or Firm—Brinks Hofer Gilson & Lione

(57) ABSTRACT

A method of treatment of a body cavity of an animal that includes inserting a portion of an insertion device into a body cavity of an animal and simultaneously supplying from the inserted insertion device a first fluid and either a medical instrument or a second fluid into the body cavity, wherein the first fluid and either the medical instrument or the second fluid are not in fluid communication with one another within the insertion device.

62 Claims, 7 Drawing Sheets

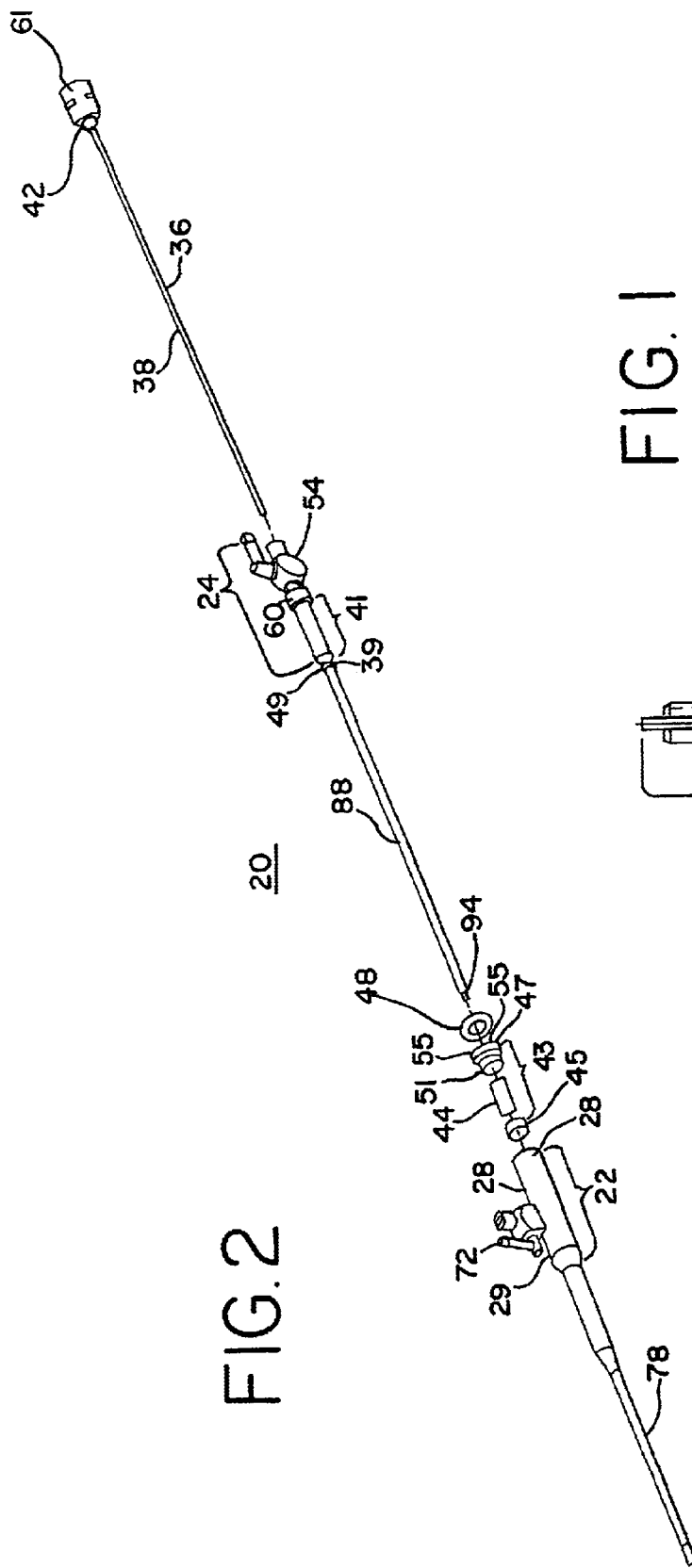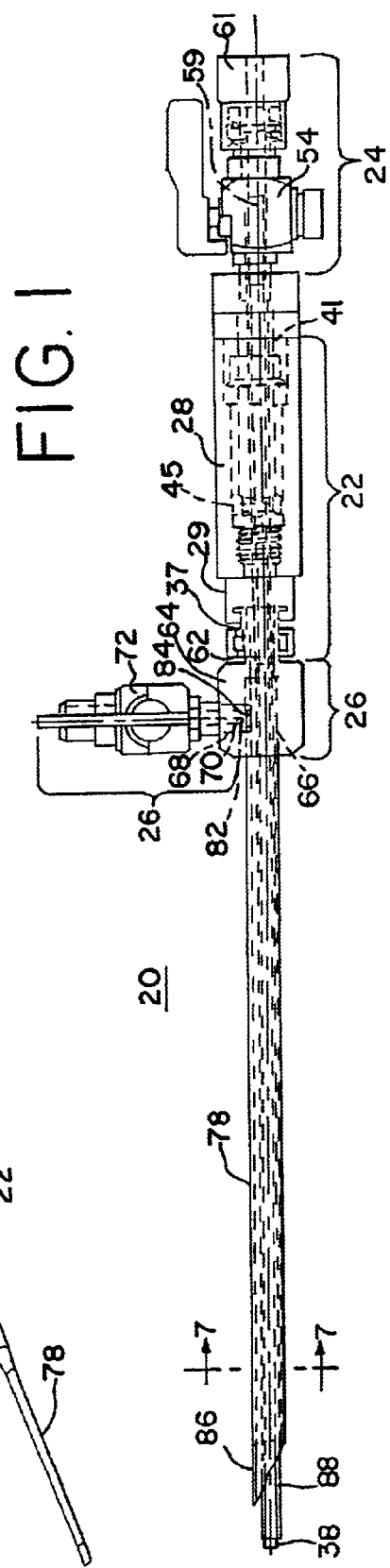

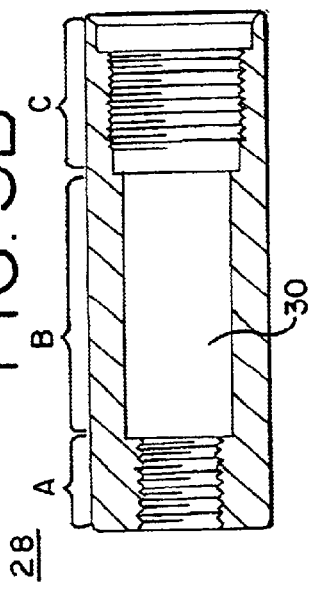
FIG. 3A
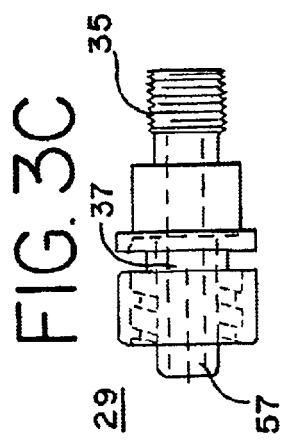
FIG. 3B
FIG. 3C
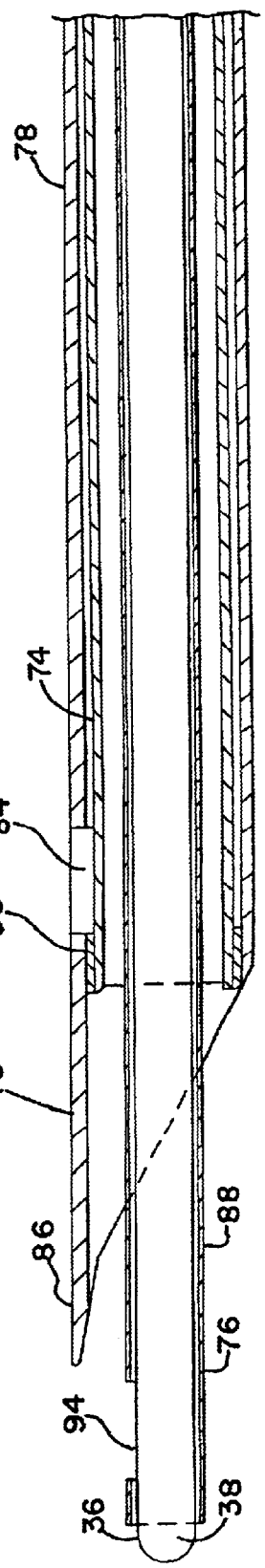
FIG. 4

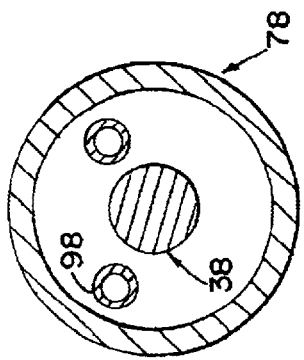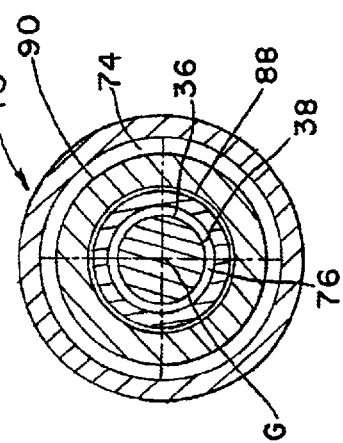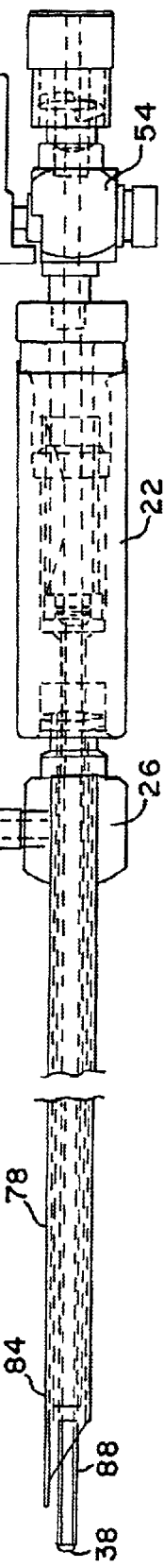

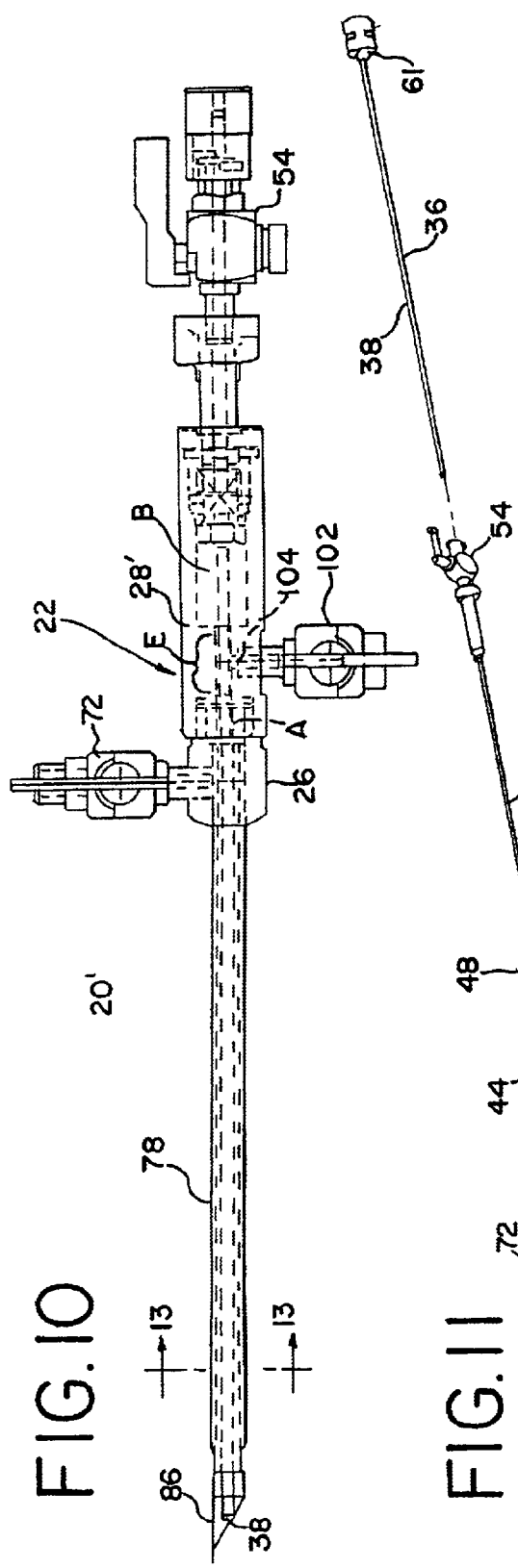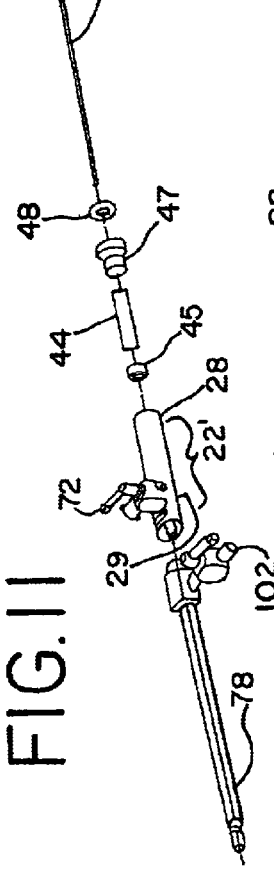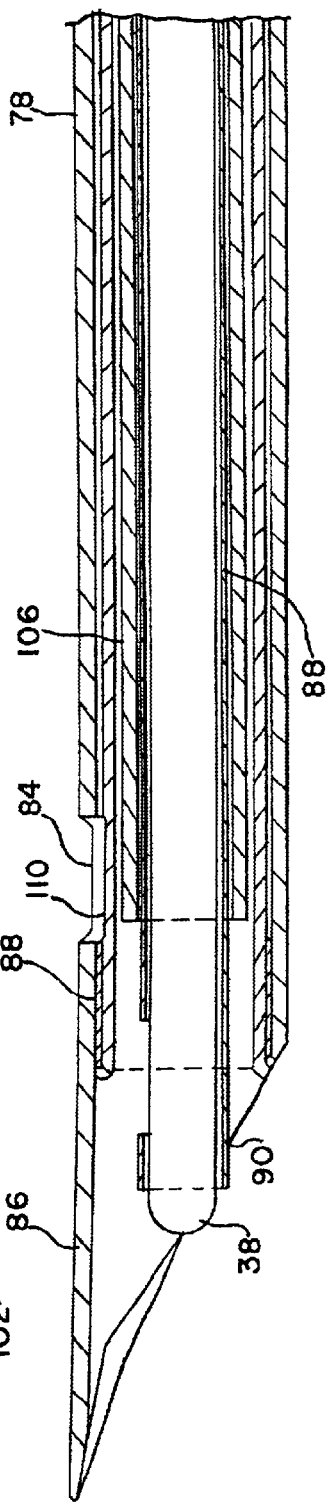

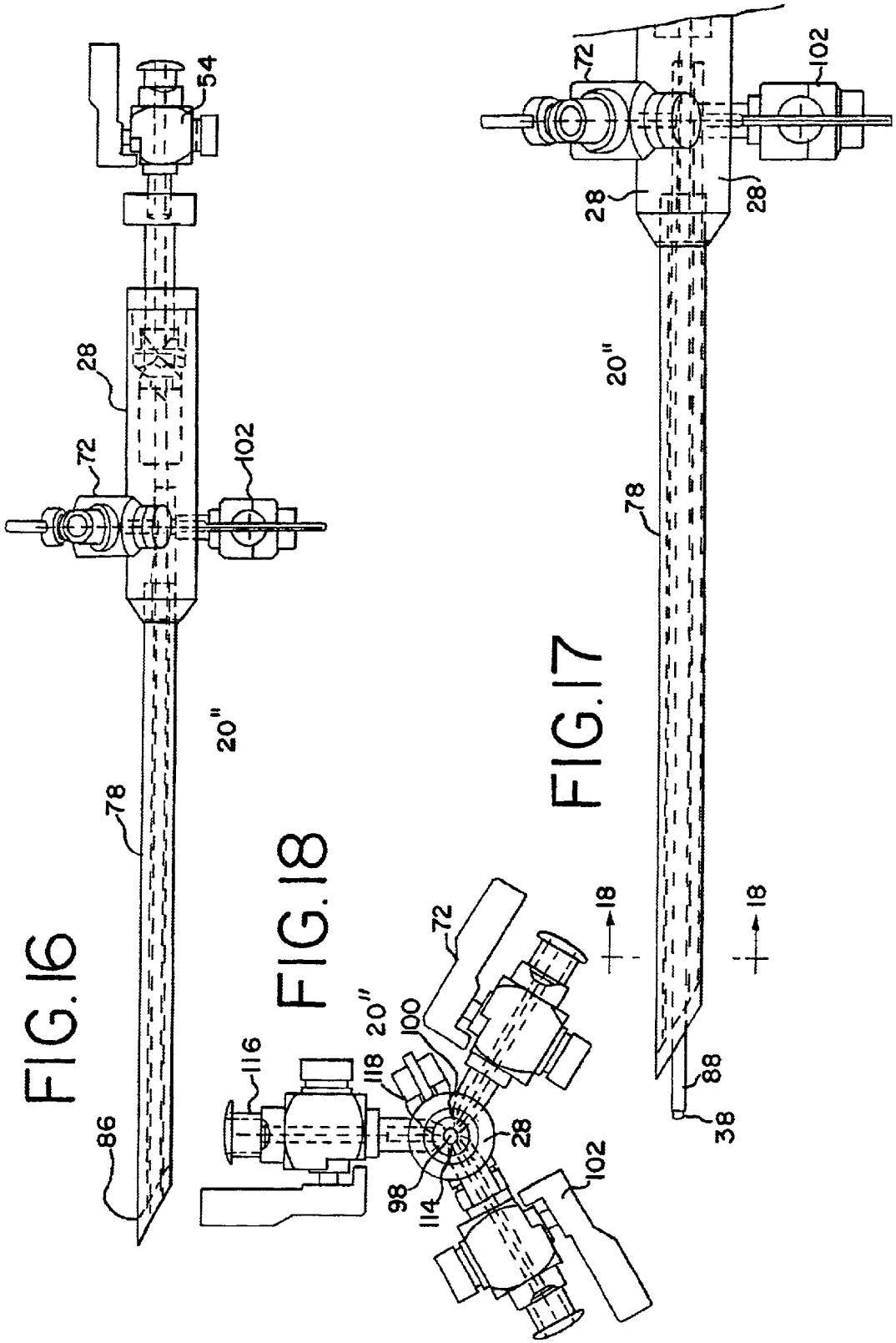

LAPAROSCOPIC INSERTION DEVICE

BACKGROUND OF THE INVENTION

1. Field of the Invention

The present invention relates generally to instruments for laparoscopic surgery. In particular, it relates to an improved laparoscopic surgical instrument that can simultaneously perform multiple tasks and procedures independent of one another.

2. Discussion of Related Art

Laparoscopic surgery involves the use of small incisions to insert surgical instruments of 3–10 millimeter (mm) diameter into the abdominal cavity. In performing such surgery, telescopes of 5–11 mm diameter usually also are inserted through the abdominal wall in order to view intraabdominal contents during the surgery. The initial step in laparoscopic surgery is to insert a needle of about 2 mm diameter through the abdominal wall such that the tip of the needle lies in the abdominal cavity itself. About 2–4 liters of a medical grade sterilized gas such as carbon dioxide, is insufflated through the needle and into the cavity. This procedure separates the abdominal wall from the organs and also usually separates the organs from one another, as the case may be.

The traditional device for passage of an insufflating gas is the Verres needle which comprises an outer cannula which has a distal needle-like tip for puncturing the abdominal wall and an expanded opposite portion which houses a spring mechanism for retraction of an inner cannula or obturator. The obturator comprises a hollow tube having an enclosed, rounded distal end with a lateral port in close proximity to the said distal end. As the Verres needle penetrates the epidermis and abdominal wall, the obturator retracts into the outer cannula against the bias of the spring to facilitate penetration through the abdominal wall. After penetration of the abdominal wall, the distal end of the obturator is spring-biased out of the Verres needle into the abdominal cavity. An insufflating gas then is delivered to the abdominal cavity from a gas supply detachably connected to the Verres needle so that the insufflating gas can enter the expanded portion of the outer cannula and traverse inside the inner cannula and enter the abdominal cavity through the lateral port located in the distal end of the inner cannula. In this case, the obturator and insufflating gas share a common passage or channel within the inner cannula. The insufflating gas serves to separate the abdominal wall from underlying organs.

In some known devices, the obturator can be removed so that a medical instrument, such as an endoscope, can be inserted into the space vacated by the obturator and inserted into the abdominal cavity. One disadvantage of the inserting the medical instrument into the Verres needle is that the medical instrument causes a significant restriction to the flow of insulating gas within the Verres needle since the medical instrument and the insufflating gas share a common passage or channel in the inner cannula. Such restriction in flow of the insufflating gas can limit the effectiveness of the insufflator.

Known trocars are similar to the above-described Verres needle in that they have a cannula that forms a single passage that contains both the insufflating gas and an obturator. One difference between a trocar and a Verres needle is that the Verres needle is typically a 14 gage needle size while trocars are known to have sizes ranging from 10 to 12 mm. One similarity between a trocar and a Verres needle is that the trocars are known that allow the obturator to be removed so that a medical device, such as an endoscope, can be inserted into the cannula. Like the Verres needle described previously, inserting the medical instrument into the cannula causes a significant restriction to the flow of insufflating gas within the trocar due to the sharing of a common passage by the medical instrument and the insufflating gas.

Another disadvantage of insertion devices, such as Verres needles and trocars, is that only one fluid can be conveyed within the insertion device at any one time. If multiple fluids are needed to be conveyed to or from the abdominal cavity for instance, then multiple Verres needles or trocars would be needed where each Verres needle or trocar is associated with only one of the multiple fluids. Using multiple insertion devices lead to the disadvantages of increasing the cost of the procedure, the complexity of the procedure and potentially increasing trauma incurred by the patient.

In the alternative, a single Verres needle or trocar could be used where one of the multiple fluids would be conveyed at one period of time and the other multiple fluids would be conveyed at separate and distinct time. Such a mode of operation could lead to contamination of the Verres needle or trocar with multiple fluids, increase the complexity of timing the application of fluids and requiring special metering and/or control devices.

SUMMARY OF THE INVENTION

One aspect of the present invention regards an insertion device that includes a housing, a first port attached to the housing for receiving a first fluid and a first chamber connected to the first port and positioned within the housing, wherein the first chamber has an opening that is in fluid communication with a target area. A second port attached to the housing for receiving a second fluid and a second chamber connected to the second port and positioned within the housing, wherein the second chamber has an opening that is in fluid communication with the target area, wherein the first chamber and the second chamber are permanently not in fluid communication with one another and simultaneously are in fluid communication with the target area.

A second aspect of the present invention regards a method of treatment of a body cavity of an animal that includes inserting a portion of an insertion device into a body cavity of an animal and simultaneously supplying from the inserted insertion device a first fluid and a second fluid into the body cavity, wherein the first fluid and the second fluid are not in fluid communication with one another within the insertion device.

A third aspect of the present invention regards a method of treatment of a body cavity of an animal that includes inserting a portion of an insertion device into a body cavity of an animal and simultaneously supplying from the inserted insertion device a fluid and a medical instrument into the body cavity, wherein the first fluid and the medical instrument are not in fluid communication with one another within the insertion device.

Each aspect of the present invention provides the advantage of improving fluid flow in an insertion device during a laparascopic procedure.

Each of the first two aspects of the present invention provides the advantage of decreasing the cost of laparoscopic procedures by using a single insertion device for simultaneously conveying multiple fluids during a laparascopic procedure.

Each of the first two aspects of the present invention provides the advantage of decreasing the complexity of laparoscopic procedures by simultaneously conveying multiple fluids during a laparascopic procedure.

Each of the first two aspects of the present invention provides the advantage of reducing the risk of contamination of an insertion device by multiple fluids conveyed by the insertion device during a laparascopic procedure.

The present invention, together with attendant objects and advantages, will be best understood with reference to the detailed description below in connection with the attached drawings.

BRIEF DESCRIPTION OF THE DRAWINGS

FIG. 1 is a side, partially transparent view of an embodiment of an insertion device in an extended mode according to the present invention;

FIG. 2 is a perspective, partially exploded view of the insertion device of FIG. 1;

FIG. 3A is a side cross-sectional view of an embodiment of a lumen sub-assembly to be used with the insertion device of FIG. 1;

FIG. 3B is a side cross-sectional view of an embodiment of a lumen housing to be used with the lumen sub-assembly of FIG. 3A;

FIG. 3C is a side cross-sectional view of an embodiment of a lumen housing adapter to be used with the lumen sub-assembly of FIG. 3A;

FIG. 4 is an enlarged side, partially transparent view of an end of the insertion device of FIG. 1 in an extended mode;

FIG. 7 is cross-sectional view of the insertion device of FIG. 1 as taken along lines 7—7 of FIG. 1;

FIG. 8 is a side, partially transparent view of a second embodiment of an insertion device in an extended mode according to the present invention;

FIG. 9 is a cross-sectional view of a third embodiment of an insertion device according to the present invention;

FIG. 10 is a side, partially transparent view of a fourth embodiment of an insertion device in a retracted mode according to the present invention;

FIG. 11 is a perspective, partially exploded view of the insertion device of FIG. 10;

FIG. 12 is an enlarged side, partially transparent view of an end of the insertion device of FIG. 10 in a retracted mode;

FIG. 16 is a side, partially transparent view of a seventh embodiment of an insertion device in a retracted mode according to the present invention;

FIG. 17 is an enlarged side, partially transparent view of the insertion device of FIG. 16 in an extended mode; and FIG. 18 is cross-sectional view of the insertion device of FIG. 16 taken along lines 18—18 of FIG. 17.

DETAILED DESCRIPTION OF THE INVENTION

Figure 5:
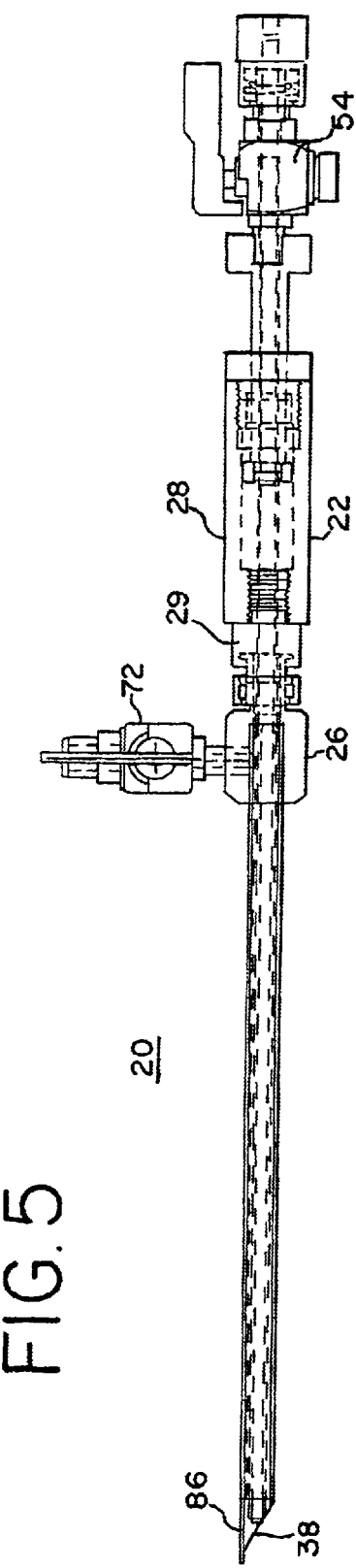
FIG. 5 is a side, partially transparent view of the insertion device of FIG. 1 in a retracted mode.

Referring now to FIGS. 1–7, an insertion device, such as Verres needle 20, includes a lumen housing sub-assembly 22, a first fluid port section 24 and a second fluid port section 26.

As shown in FIGS. 1, 2, 3A–B and 5, the lumen housing sub-assembly 22 includes a cylindrical-like lumen housing 28 that is threadedly attached to a lumen housing adapter 29. As shown in FIGS. 3A–B, the lumen housing 28 includes a central channel 30 that extends from a distal end 32 to a proximal end 34 of the lumen housing 28. The central channel 30 has a length of approximately 1.437 inches. The channel 30 has a diameter that varies in a step-like manner. For example, the channel 30 has four distinct portions: 1) a distal portion A that has a diameter of approximately 0.36 inches and a length of approximately 0.312 inches, 2) an intermediate distal portion B that has a diameter of approximately 0.302 inches and a length of approximately 0.725 inches, an intermediate proximate portion C that has a diameter of approximately 0.302 inches and a length of approximately 0.40 inches, and a proximal portion D that has a diameter of approximately 0.5 inches and a length of approximately 0.158 inches.

The portion A of the central channel 30 is threaded, receives and is attached to a threaded male member 35 of a lumen housing adapter 29 as shown in FIG. 3A. The lumen housing adapter 29 has an opening 37 that is aligned with the channel 30 of the lumen housing 28. The attached lumen housing adapter 29 and lumen housing 28 constitute the lumen housing sub assembly 22. Note that a distal end 57 of the lumen housing adapter 29 is attached via silver solder to a needle cannula exterior housing 78. As shown in FIGS. 1, 2 and 4–7, the housing 78 is substantially cylindrical/annular in shape having a length of approximately 4.970 inches, an inner diameter of approximately 0.173 inches and an outer diameter of approximately 0.203 inches. The housing 78 has a 0.093 inch diameter opening 80 that is aligned with an opening 82 of the fluid port section 26. The opening 80 is approximately 0.24 inches from a proximal end of the housing 78. The housing 78 has a second opening 84 formed approximately 4.09 inches from the opening 80 and further includes a needle 86 formed at a distal end thereof. The housing 78 is preferably made of stainless steel.

As shown in FIGS. 1, 2 and 5, the portions A-D of the central channel 30 and the opening 37 receive an inner needle cannula wall 88 that is inserted into and welded into an opening 39 of a cylindrical-like extension 41 of a port, such as stopcock 54, that forms part of the fluid port section 24. The inner needle cannula wall 88 is annular/cylindrical in shape having a length of approximately 7.282 inches, an inner diameter of approximately 0.84 inches and an outer diameter of approximately 0.93 inches. As shown in FIGS. 1, 2 and 4–6, the inner needle cannula wall 88 is inserted into the interior of the housing 78 and has a distal end that is near the distal end of the housing 78.

As shown in FIG. 2, the inner needle cannula wall 88 is also inserted into an O-ring seal 48 and a bias mechanism 43 that includes a spring 44, a stop 45 and a compression piece 47. In particular, the inner needle cannula wall 88 is inserted into aligned openings of the O-ring seal 48, the compression piece 47, the spring 44 and the stop 45. Once the inner needle cannula wall 88 is inserted, the stop 45 is threaded onto a threaded end portion 49 of the extension 41 of the fluid port section 24. At this stage, the extension 41 passes through the aligned openings of the spring 44, compression piece 47 and O-ring seal 48. The extension 41 is inserted into channel 30 of the lumen housing 28 and the compression piece 47 is inserted into portion C of channel 30 of the lumen housing 28. The exterior threads 51 of the compression piece 47 threadedly engage the threads 53 of portion C of channel 30. The end result of the threaded attachment of stop 45 and compression piece 47 is that the spring 44 is captured between the stop 45 and compression piece 47. In addition, the lumen housing 28 is able to slidingly move relative to the fluid port section 24 along the longitudinal length of the extension 41. Such movement is limited in that the compression piece 47 attached to the lumen housing 28 is constrained to move from where the stop 45 is attached to extension 41 to where the O-ring seal 48 that is welded to an annular shoulder 60 of the extension 41. The O-ring seal 48 seals the space between lumen housing 28 and extension 41 when a proximal end 55 of the compression piece 47 abuts against the O-ring seal 48.

After the lumen housing 28 is attached to the fluid port section 24 via bias mechanism 43, an annular-like stainless steel wall 36 of an obturator 38 is inserted into a longitudinal channel 59 formed in the fluid port section 24. The obturator 38 has a length of approximately 8.75 inches and a diameter of approximately 0.063 inches. As shown in FIG. 2, the obturator 38 has a rounded distal end 40. As shown in FIGS. 1, 2 and 5, the proximal end 42 of the obturator 38 is attached via silver solder to a cap 61. The cap 61 has threads that engage a proximal end of the stopcock 54. The cap 61 prevents the obturator 38 from exiting the distal end of the housing 78. As shown in FIGS. 1, 2 and 4–6, the obturator 38 is inserted into the interior of the inner needle cannula wall 88 and has a distal end that is near the distal end of the housing 78.

With the obturator 38 positioned within the inner needle cannula wall 88 and the housing 78, the Verres needle 20 allows for both the obturator 38 and the inner needle cannula wall 88 to be movable relative to the housing 78 from an extended position to a retracted position and vice versa. In the case of the extended position, when no forces are pushing the inner cannula wall 88 toward the proximal end of the Verres needle 20, the spring 44 is maintained at its natural length and so the distal end of the inner cannula wall 88 extends past the housing 78 as shown in FIGS. 1 and 4. Thus, the spring 44 normally biases the inner needle cannula wall 88 to an extended position shown in FIGS. 1 and 4. When no forces are pushing the obturator toward the proximal end of the Verres needle 20, the obturator 38 also extends past the housing 78 as shown in FIGS. 1 and 4. Note that when the inner needle cannula wall 88 is at the extended position, the proximal end 55 of the compression piece 47 seals the O-ring 48 between itself and the shoulder 60.

Figure 6:
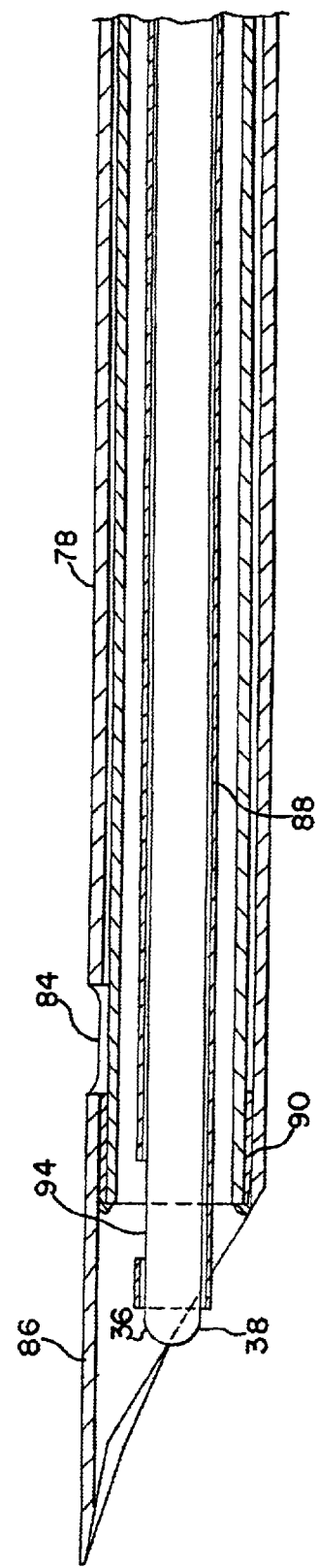
FIG. 6 is an enlarged side, partially transparent view of an end of the insertion device of FIG. 1 in a retracted mode.

The retracted position is achieved when a force pushes the inner cannula wall 88 toward the proximal end of the Verres needle 20. Such pushing causes the distal end of the inner cannula wall 88 to enter into the housing 78 and causes the stop 45 and the distal end of the spring 44 to move toward the proximal end of the Verres needle 20 as shown in FIG. 5. This causes the spring 44 to be compressed. When a force pushes the obturator toward the proximal end of the Verres needle 20, the distal end of the obturator 38 also enters into the housing 78 as shown in FIGS. 5 and 6.

As shown in FIGS. 1 and 3, the second fluid port section 26 has a threaded male member 62 that engages threads 63 formed in the distal portion 57 of the lumen housing adapter 29. The threaded male member 62 is integrally attached to a body 64 that includes an axially extending channel 66 and a radially extending channel 68.

The radially extending channel 68 is threaded and is in fluid communication with the axially extending channel 66. As shown in FIGS. 1 and 5, a threaded male member 70 of a port, such as stopcock 72, is inserted into and threadedly engages the channel 68.

The stopcocks 54 and 72 preferably are attached to supplies (not shown) for two isolated fluids. Thus, the stopcocks 54 and 72 allow for two different fluids, to be supplied to the Verres needle 20. For example, stopcocks 54 and 72 can be attached to separate supplies of carbon dioxide. In another embodiment, one of the stopcocks 54 can be attached to a supply of carbon dioxide while the other stopcock is attached to a supply of an aerosolized medication. In accordance with the present invention, the two fluids are permanently not in fluid communication with one another. Note that in this application, the term fluid is deemed to include either a gas or a liquid.

Isolation between the two fluids is accomplished by a pair of chambers 74 and 76 that are formed within the needle cannula exterior housing 78. The annular chamber 74 is defined as the space between the housing 78 and a cannula wall 90. The cannula wall 90 is annular/cylindrical in shape having a length of approximately 4.562 inches, an inner diameter of approximately 0.134 inches and an outer diameter of approximately 0.165 inches. The cannula wall 90 is attached to housing 78 by silver solder. In particular, silver solder is applied to the housing 78 and wall 90 distally of the opening 84. Silver solder is also applied to the housing 78 and wall 90 proximally of opening 82. The silver solder seals the chamber 74 at distal and proximal ends thereof. As shown in FIG. 7, the housing 78 and the wall 90 are concentric about a common axis G so that the annular chamber 74 is concentric about axis G as well. The housing 78 and the wall 90 are spaced from one another by approximately 0.080 inches.

In operation, the stopcock 72 is opened so that a fluid is received by the opening 82 and delivered into the opening 80 of the housing 78. The fluid then flows into the chamber 74 and exits out of the opening 84 of the housing and the annular space 74 between housing 78 and wall 90 and flows into a target area, such as a body cavity or abdomen. Thus, the opening 84 is in fluid communication with a target area.

A second annular chamber 76 is defined as the space between an annular portion of the wall 36 of the obturator 38 and an inner needle cannula wall 88. As shown in FIG. 5, the wall 36 and the cannula wall 88 are concentric about axis G so that the annular chamber 76 is concentric about axis G as well. The wall 36 and the cannula wall 88 are spaced from one another by approximately 0.021 inches. In addition, the wall 88 is movable relative to the housing 78 in that it is attached to the extension 41 of the stopcock 54, which is biased via spring 44 so as to move relative to the housing 78. As mentioned previously, the obturator 38 and wall 36 are attached to the stopcock 54 as well via cap 51. Thus, when stopcock 54 and wall 88 move relative to housing 78, the obturator 38 and wall 36 will also move with stopcock 54 and so move in unison with the wall 88.

As shown in FIGS. 1 and 4–6, the obturator 38, the cannula wall 88 and the annular chamber 76 extend from the distal end of the Verres needle 20 to a distal opening 39 formed in the stopcock 54. In operation after the Verres needle 20 is inserted into the body cavity or abdomen and the obturator 38 is removed after the cap 61 is unthreaded and attached from the stopcock 54, the stopcock 54 remains open so that a fluid is received by the opening 59 and delivered into the annular chamber 76. The fluid then flows the entire length of the chamber 76 and exits a distal opening 94 and the distal end of the chamber 76 and flows into a target area, such as a body cavity or abdomen. Thus, the opening 94 and the distal end of the chamber 76 are in fluid communication with a target area.

When both stopcock 54 and 72 are open at the same time, the fluids associated with the stopcocks flow within the Verres needle 20 do not intermingle within the needle 20 since the annular walls 78 and 90 do not define a volume of space that is common with any volume of space defined by the annular walls 36 and 88. Accordingly, the chambers 74 and 76 are isolated from one another so they are permanently not in fluid communication with one another. The fluids are then expelled out of the Verres needle 20 into the target area so that the chambers 74 and 76 simultaneously are in fluid communication with the target area.

The Verres needle 20 described above with respect to FIGS. 1–7 can be used in a variety of medical procedures to be performed on an animal, such as a human being. In a typical method of treatment, the needle 86 of the housing 78 is used pierce an area of a human patient. During the piercing, the obturator 38 and the cannula wall 88 are pushed by the patient's tissue to a retracted position as shown in FIGS. 5 and 6. Such pushing causes spring 44 to compress as well. Once the needle 86 enters a target area, such as the chest cavity or the abdomen of the human patient, the pressure exerted by the tissue is absent causing spring 44 to expand which results in cannula wall 88 to move to the extended position shown in FIGS. 1 and 4. Since the obturator 38 is mechanically joined to the cannula wall 88, the obturator 38 also moves to the extended position once the needle 86 enters the target area. Upon noticing that the obturator 38 has moved to the extended position, the surgeon determines that the Verres needle 20 has entered into the abdomen whereupon the cap 61 is unthreaded from the stopcock 54, the obturator 38 is removed and an insufflation gas is then directed into the abdomen by opening up either stopcock 54 or 72. With the obturator 38 retained or removed, fluids can be delivered or received within space 74 by utilizing stopcock 72.

The insufflation gas expands the abdomen so that laparoscopic procedures and monitoring can be performed. For example, while the insufflation gas is supplied to the chest cavity or abdomen via chamber 74, for example, the other chamber 76 can be used to simultaneously perform a continuous pressure measurement of the peritoneum. This allows for faster insufflation because the pressure would be read continuously and the insufflator would flow gas continuously to the body cavity via chamber 74 instead of in a stop and start mode that is currently used.

In another mode of operation during insufflation via chamber 74, the other chamber 76 can be adapted to receive a medical instrument by the open stopcock 54 and removing the obturator 38 when access to that space is required. Possible medical instruments that can be fed into chamber 76 into the abdomen are: 1) fluid pumps, such as hand pumps, syringe pumps, peristaltic pumps, centrifugal pumps, etc., 2) wall suction, or portable vacuum suction pumps, 3) graspers, scissors, electro-surgical tools, suction/irrigation wands, regular or mini endoscopes, etc., 4) catheters (such as aerosolization ala TMI), 5) infusion devices (gravity fluid bags), syringe injection, biopsy needles etc., 6) humidification devices (evaporative media), and 7) filtering devices, passive (filter media) or active (withdraw a fluid, filter it, and replace it). An example of using a filtering device is shown in FIG. 8 where a filter 96 is attached to stopcock 72 in a well known manner.

Besides the medical instruments mentioned above that treat the abdomen, monitoring devices can be connected to the chamber 76, such as 1) pressure relief valves, passive (mechanical) or controlled (electronic) pressure transducers, 2) thermocouples, RTD's, thermistors, etc (temperature), 3) CCD cameras, chip (solid state) cameras, and 4) ultrasonic, and humidity measuring devices.

Note that depending on the particular instrument or monitoring involved mentioned above, the stopcock 54 of chamber 76 can be replaced by or used in conjunction with well known rubber seals, injection ports, flap valves and iris valves.

There are many ways in which the Verres needle 20 of FIGS. 1–7 can be used. The matrix set forth below shows some of the many possibilities in which the Verres needle 20 conducts a number different functions and or use of devices to enhance medical techniques. Note that the columns of the matrix indicate possible applications that can be performed by one of the ports 54, 72 while the rows indicate applications that can be performed by the other port. An X indicates that the applications for the corresponding row and column can be performed simultaneously. Although the matrix would indicate that only two of the categories would be used in conjunction which each other, in reality, as many of these could be used in combination as is practical to design the introducer (three, four, or five, etc) if the operative area would allow for one device to be used.

|  | Infusing gas | Infusing liquid | Suctioning Gas | Suctioning liquid | Venting or pressure relief | Tool entry (instrument) | Catheter entry |
|---|---|---|---|---|---|---|---|
| Infusing gas | — | X | X | X | X | X | X |
| Infusing liquid | X | — | X | X | X | X | X |
| Suctioning gas | X | X | — | X | X | X | X |
| Suctioning liquid | X | X | X | — | X | X | X |
| Venting or pressure relief | X | X | X | X | — | X | X |
| Tool entry (instrument) | X | X | X | X | X | — | X |
| Catheter entry | X | X | X | X | X | X | — |
| Measure pressure | X | X | X | X | X | X | X |
| Measure Temperature | X | X | X | X | X | X | X |
| Measure Flow | X | X | X | X | X | X | X |
| Endoscopic port | X | X | X | X | X | X | X |
| Camera (chip) port | X | X | X | X | X | X | X |
| Medication infusion | X | X | X | X | X | X | X |
| Moisture infusion | X | X | X | X | X | X | X |

In summary, the isolated chambers 74 and 76 allow for multiple fluids to be conveyed to a target area. The isolated chambers 74 and 76 allow for a fluid to be supplied to the target area via one chamber while the other chamber simultaneously receives a fluid from the target area. The isolated chambers 74 and 76 also allow for simultaneous supply to or removal of a fluid from a target area while a medical instrument is supplied to the target area via the other chamber. The isolated chambers 74 and 76 allow for simultaneous use of medical instruments and/or monitor devices in the target area. Note that when a medical instrument or monitor device is to be inserted into chamber 76, the obturator 38 can be removed in a well known manner so as to increase the volume of the chamber 76.

While the above description regards using isolated chambers 74 and 76 that are annular and concentric, it is possible to replace the annular walls 88 and 90 of FIGS. 1–8 with separate and nonintersecting tubes 98 and 100 that are shown in FIG. 9. The tube 98 extends from the opening 92 to the distal end of the housing 78. Similarly, tube 100 extends from the opening 80 to the distal end of the housing 78. The tubes 98 and 100 are preferably made of stainless steel or plastic and have a diameter of approximately 0.160 inches. When made of stainless steel, the tubes 98 and 100 are attached to the housing 78 by silver solder. When made of plastic, the tubes 98 and 100 are adhesively bonded to the housing 78.

It is possible to simultaneously apply more than two fluids and/or medical instruments to a target area. This is accomplished by a Verres needle 20' as shown in FIGS. 10–13. In this embodiment, the Verres needle 20 of FIGS. 1–7 is altered so that a third port, such as stopcock 102, is attached to the lumen housing 28' via a threaded attachment. The stopcock 102 has an opening 104 that is in fluid communication with the portion B of central channel 30 of the lumen housing 28'. The stopcock 102 allows for a third fluid to be received by the Verres needle 20'. Note that lumen housing 28' of FIG. 10 differs from lumen housing 28 of FIG. 1 in that the lumen housing 28' is lengthened to accommodate the extra stopcock 102 and so a portion E of channel 30 connecting portions A and B is added.

Figure 13:
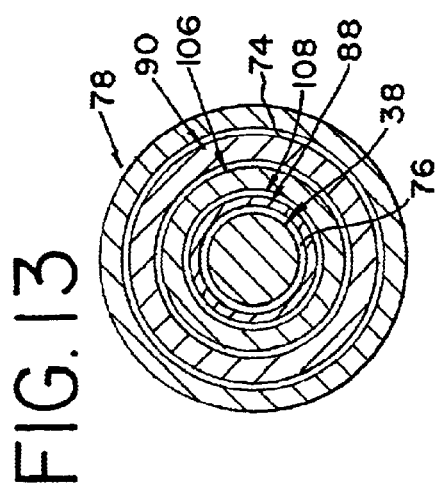
FIG. 13 is a cross-sectional view of the insertion device of FIG. 10 as taken along lines 13—13 of FIG. 10.

Isolation between the three fluids is accomplished in part by chambers 74 and 76 as described previously with respect to the Verres needle 20 of FIGS. 1–7. Isolation between the fluid received by stopcock 102 is accomplished by a stationary cannula wall 106 that is positioned within the needle cannula exterior housing 78. The wall 106 is attached to obturator 88 proximally of the opening 104 of the stopcock 102. As shown in FIGS. 12 and 13, the wall 106 is substantially cylindrical/annular in shape having a length of approximately 4.5 inches, an inner diameter of approximately 0.094 inches and an outer diameter of approximately 0.12 inches. The wall 106 and wall 88 define an annular chamber 108 therebetween. The annular wall 88 has a length of approximately 6.75 inches, an inner diameter of approximately 0.73 inches and an outer diameter of approximately 0.84 inches. The separation between walls 88 and 106 is approximately 0.041 inches.

Regarding the formation of the chambers 74 and 76, the annular wall 90 has a length of approximately 7.28 inches, an inner diameter of approximately 0.134 inches and an outer diameter of approximately 0.165 inches. The housing 78 and the wall 90 are spaced from one another by approximately 0.041 inches.

In operation, the stopcock 102 is opened so that a fluid is received by the opening 104 and delivered into the portion E of channel 30. The fluid then flows into portion A of channel 30 and into the chamber 108 positioned between walls 88 and 106. The fluid then flows out of an opening 110 formed in wall 88, exits out of the opening 84 of the housing 78 and flows into a target area, such as a body cavity. The opening 110 is aligned with the opening 84.

When all three stopcock 54, 72 and 102 are open at the same time, the fluids associated with the stopcocks flow within the Verres needle 20 do not intermingle within the needle 20 since the chambers 74, 76 and 108 are isolated from one another so they are permanently not in fluid communication with one another. The fluids are then expelled out of the Verres needle 20' into the target area so that the chambers 74, 76 and 108 simultaneously are in fluid communication with the target area.

Figure 14:
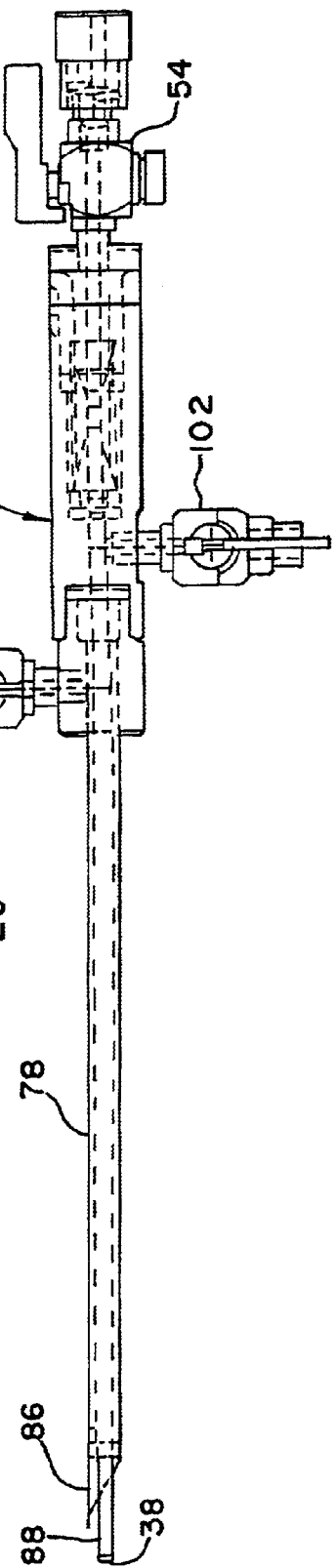
FIG. 14 is a side, partially transparent view of a fifth embodiment of an insertion device in an extended mode according to the present invention.

The Verres needle 20' described above with respect to FIGS. 10–13 can be used in a variety of medical procedures, such as those described previously with respect to the Verres needle of FIGS. 1–7. For example, a pressure relief valve 112 can be connected to any of the ports, such as stopcock 72 as shown in FIG. 14 so as to permit the escape of gas in case of an over pressure situation. Other functions that could be performed by stopcock 72 are applying suction to chamber 108 to remove a fluid, providing a filtered exit port to allow smoke removal during electro surgical procedures, positioning an endoscope or an instrument through one of the other ports.

It should be noted that the matrix of applications discussed previously with respect to the Verres needle 20 of FIGS. 1–7 is applicable to the Verres needle 20' of FIGS. 10–13 in that the stopcock 102 can perform any one of the applications in the column of the matrix simultaneously with any dual application combination for stopcocks 54 and 72 as defined by the matrix.

Figure 15:
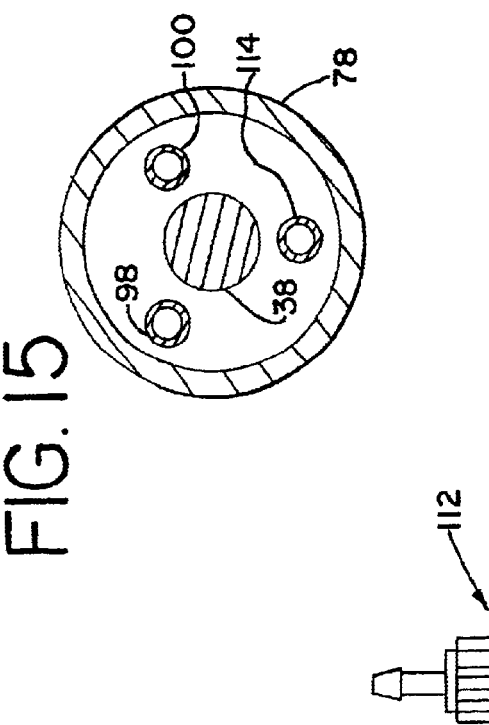
FIG. 15 is a cross-sectional view of a sixth embodiment of an insertion device according to the present invention.

While the above description regards using isolated chambers 74, 76 and 108 that are annular and concentric, it is possible to replace the annular walls 88, 90 and 106 with separate and nonintersecting tubes 98, 100 and 114 that are shown in FIG. 15. The tube 98 extends from the opening 92 to the distal end of the housing 78. Tube 100 extends from the opening 80 to the distal end of the housing 78. Similarly, tube 114 extends from portion A of channel 30 to the distal end of the housing 78. The tubes 98, 100 and 114 are preferably made of stainless steel or plastic and have a diameter of approximately 0.098. When made of stainless steel, the tubes 98 and 100 are attached to thee housing 78 by silver solder. When made of plastic, the tubes 98 and 100 are adhesively bonded to the housing 78.

Another embodiment of a Verres needle that uses separate and nonintersecting tubes is shown in FIGS. 16–18. In this embodiment, the Verres needle 20" varies from the Verres needle 20' of FIG. 10 in that the stopcock 72 is now attached to the main body 28 and a fourth stopcock 116 is attached to the main body 28 as well. Thus, four fluids can be received simultaneously by the needle 20". As shown in FIG. 18, the stopcocks 72, 102 and 116 are spaced from one another by approximately 120°. The stopcock 116 has a tube 118 that is connected to it and that extends to the distal end of the housing 78. The tube 118 has a length of approximately 4.9 inches and diameter of approximately 0.098 inches that is the same as tubes 100 and 114. As shown in FIG. 18, the tube 98 is centrally located within main body 28 and the remaining tubes 100, 114 and 118 are each spaced 0.040 inches from the center of tube 98 and are spaced 120° relative to one another.

The foregoing description is provided to illustrate the invention, and is not to be construed as a limitation. Numerous additions, substitutions and other changes can be made to the invention without departing from its scope as set forth in the appended claims. For example, the present invention can be applied to other insertion devices, such as trocars, where the trocar is inserted into an opening of an animal, such as a human patient, and the opening was formed by an instrument separate from the trocar. In addition, the invention can be used in many fields of medicine, such as minimally invasive surgery, arthroscopy, urology, neurology, gynecology, gastroenterology, general surgery, anesthesiology, cardiology and internal medicine.

We claim:

1. An insertion device comprising:
   a housing;
   a first port attached to said housing for receiving a first fluid;
   a first chamber connected to said first port and positioned within said housing, wherein said first chamber has an opening that is in fluid communication with a target area;
   an annular wall inserted within said housing, wherein said annular wall defines at least in part said first chamber, wherein said annular wall is movable relative to said housing and a distal end of said annular wall is substantially rigid and is able to move beyond said housing;
   a second port attached to said housing for receiving a second fluid; and
   a second chamber connected to said second port and positioned within said housing, wherein said second chamber has an opening that is in fluid communication with said target area, wherein said first chamber and said second chamber are permanently not in fluid communication with one another and simultaneously are in fluid communication with said target area.

2. The insertion device of claim 1, further comprising a spring that engages said annular wall and said housing.

3. The insertion device of claim 1, further comprising a second annular wall inserted within said housing and within said annular wall, wherein said annular wall and said second annular wall define said second chamber.

4. The insertion device of claim 1, further comprising:
   a third port attached to said housing for receiving a third fluid; and
   a third chamber connected to said third port and positioned within said housing, wherein said third chamber has an opening that is in fluid communication with said target area, wherein said third chamber, said second chamber and said first chamber are permanently not in fluid communication with one another and simultaneously are in fluid communication with said target area.

5. The insertion device of claim 4, further comprising a second annular wall inserted within said housing and within said annular wall, wherein said annular wall and said second annular wall define said second chamber.

6. The insertion device of claim 5, further comprising a third annular wall inserted within said housing and within said second wall, wherein said third annular wall and said second annular wall define said third chamber.

7. The insertion device of claim 2, further comprising a second annular wall inserted within said housing, wherein said annular wall does not define a volume of space that is common with any volume of space defined by said second annular wall.

8. The insertion device of claim 7, further comprising a third annular wall inserted within said housing, wherein said third annular wall does not define a volume of space that is common with any volume of space defined by either said annular wall and said second annular wall.

9. The insertion device of claim 1, wherein said housing comprises a needle formed at one end thereof.

10. The insertion device of claim 4, wherein said housing comprises a needle formed at one end thereof.

11. The insertion device of claim 1, wherein a first gas is present within said first chamber and a second gas is present within said second chamber.

12. The insertion device of claim 11, wherein said first gas comprises carbon dioxide and said second gas comprises carbon dioxide.

13. The insertion device of claim 1, wherein said first fluid comprises carbon dioxide and said second fluid comprises an aerosolized medication.

14. The insertion device of claim 1, further comprising a pressure transducer in fluid communication with said first port.

15. The insertion device of claim 1, further comprising a pressure relief valve in fluid communication with said first port.

16. The insertion device of claim 1, further comprising a filter in fluid communication with said first port.

17. An insertion device comprising:
   a housing means for receiving a first fluid and a second fluid;
   a first port means for receiving a first fluid;
   a first chamber means for being in fluid communication with a target area wherein, said first chamber means comprises an annular wall inserted within said housing means and movable relative to said housing, wherein said annular wall comprises a distal end that is rigid and is able to move beyond said housing;
   a second port means for receiving a second fluid; and
   a second chamber means for being in fluid communication with said target area, wherein said first chamber and said second chamber are permanently not in fluid communication with one another and simultaneously are in fluid communication with said target area.

18. The insertion device of claim 17, wherein said second chamber means comprises a second annular wall inserted within said housing means.

19. The insertion device of claim 18, wherein said annular wall does not define a volume of space that is common with any volume of space defined by said second annular wall.

20. The insertion device of claim 17, further comprising:
   a third port means for receiving a third fluid; and
   a third chamber means for being in fluid communication with said target area, wherein said third chamber mean, said second chamber means and said first chamber means are permanently not in fluid communication with one another and simultaneously are in fluid communication with said target area.

21. The insertion device of claim 20, wherein said second chamber means comprises a second annular wall inserted within said housing means.

22. The insertion device of claim 21, wherein said third chamber means comprises a third annular wall inserted within said housing means and within said second annular wall, wherein said third annular wall and said second annular wall define said third chamber means.

23. The insertion device of claim 17, wherein a first gas is present within said first chamber means and a second gas is present within said second chamber means.

24. The insertion device of claim 23, wherein said first gas comprises carbon dioxide and said second gas comprises carbon dioxide.

25. The insertion device of claim 17, wherein said first fluid comprises carbon dioxide and said second fluid comprises an aerosolized medication.

26. The insertion device of claim 17, further comprising a pressure transducer in fluid communication with said first port means.

27. The insertion device of claim 17, further comprising a pressure relief valve in fluid communication with said first port means.

28. The insertion device of claim 17, further comprising a filter in fluid communication with said first port means.

29. The insertion device of claim 9, wherein said needle has a distal end that defines a surface that is sufficiently sharp to pierce the skin of a patient and enter a cavity within the patient.

30. The insertion device of claim 29, further comprising an obturator that is movable relative to said housing.

31. The insertion device of claim 30, wherein said obturator is positioned within said annular wall.

32. The insertion device of claim 10, wherein said needle has a distal end that defines a surface that is sufficiently sharp to pierce the skin of a patient and enter a cavity within the patient.

33. The insertion device of claim 1, further comprising a needle that has a distal end that defines a surface that is sufficiently sharp to pierce the skin of a patient and enter a cavity within the patient.

34. The insertion device of claim 1, further comprising an obturator that is movable relative to said housing.

35. The insertion device of claim 34, wherein said obturator is positioned within said annular wall.

36. The insertion device of claim 17, wherein said housing comprises a needle formed at one end thereof.

37. The insertion device of claim 36, wherein said needle has a distal end that defines a surface that is sufficiently sharp to pierce the skin of a patient and enter a cavity within the patient.

38. The insertion device of claim 37, further comprising an obturator that is movable relative to said housing.

39. The insertion device of claim 38, wherein said obturator is positioned within said annular wall.

40. The insertion device of claim 17, further comprising a needle that has a distal end that defines a surface that is sufficiently sharp to pierce the skin of a patient and enter a cavity within the patient.

41. The insertion device of claim 17, further comprising an obturator that is movable relative to said housing.

42. The insertion device of claim 41, wherein said obturator is positioned within said annular wall.

43. An insertion device comprising:
  a housing;
  a first port attached to said housing for receiving a first fluid;
  a first chamber connected to said first port and positioned within said housing, wherein said first chamber has an opening that is in fluid communication with a target area;
  an annular wall inserted within said housing, wherein said annular wall defines at least in part said first chamber, wherein said annular wall comprises a distal end of said annular wall is substantially rigid and is capable of being positioned beyond said housing;
  a second port attached to said housing for receiving a second fluid; and
  a second chamber connected to said second port and positioned within said housing, wherein said second chamber has an opening that is in fluid communication with said target area, wherein said first chamber and said second chamber are permanently not in fluid communication with one another and simultaneously are in fluid communication with said target area.

44. The insertion device of claim 43, further comprising a second annular wall inserted within said housing and within said annular wall, wherein said annular wall and said second annular wall define said second chamber.

45. The insertion device of claim 43, further comprising:
  a third port attached to said housing for receiving a third fluid; and
  a third chamber connected to said third port and positioned within said housing, wherein said third chamber has an opening that is in fluid communication with said target area, wherein said third chamber, said second chamber and said first chamber are permanently not in fluid communication with one another and simultaneously are in fluid communication with said target area.

46. The insertion device of claim 45, wherein said housing comprises a needle formed at one end thereof.

47. The insertion device of claim 45, further comprising a second annular wall inserted within said housing and within said annular wall, wherein said annular wall and said second annular wall define said second chamber.

48. The insertion device of claim 47, further comprising a third annular wall inserted within said housing and within said second wall, wherein said third annular wall and said second annular wall define said third chamber.

49. The insertion device of claim 43, wherein said housing comprises a needle formed at one end thereof.

50. The insertion device of claim 49, wherein said needle has a distal end that defines a surface that is sufficiently sharp to pierce the skin of a patient and enter a cavity within the patient.

51. The insertion device of claim 43, further comprising a spring that engages said annular wall and said housing.

52. The insertion device of claim 51, further comprising a second annular wall inserted within said housing, wherein said annular wall does not define a volume of space that is common with any volume of space defined by said second annular wall.

53. The insertion device of claim 52, further comprising a third annular wall inserted within said housing, wherein said third annular wall does not define a volume of space that is common with any volume of space defined by either said annular wall and said second annular wall.

54. The insertion device of claim 43, wherein a first gas is present within said first chamber and a second gas is present within said second chamber.

55. The insertion device of claim 54, wherein said first gas comprises carbon dioxide and said second gas comprises carbon dioxide.

56. The insertion device of claim 43, wherein said first fluid comprises carbon dioxide and said second fluid comprises an aerosolized medication.

57. The insertion device of claim 43, further comprising a pressure transducer in fluid communication with said first port.

58. The insertion device of claim 43, further comprising a pressure relief valve in fluid communication with said first port.

59. The insertion device of claim 43, further comprising a filter in fluid communication with said first port.

60. The insertion device of claim 43, further comprising a needle that has a distal end that defines a surface that is sufficiently sharp to pierce the skin of a patient and enter a cavity within the patient.

61. The insertion device of claim 43, further comprising an obturator that is movable relative to said housing.

62. The insertion device of claim 61, wherein said obturator is positioned within said annular wall.

* * * * *